(12) United States Patent
Machida

(10) Patent No.: US 8,092,372 B2
(45) Date of Patent: Jan. 10, 2012

(54) INSERTION ASSISTING TOOL FOR ENDOSCOPE AND ENDOSCOPE OPERATING METHOD

(75) Inventor: Mitsunori Machida, Saitama (JP)

(73) Assignee: Fujifilm Corporation, Tokyo (JP)

( * ) Notice: Subject to any disclaimer, the term of this patent is extended or adjusted under 35 U.S.C. 154(b) by 508 days.

(21) Appl. No.: 11/013,380

(22) Filed: Dec. 17, 2004

(65) Prior Publication Data

US 2005/0137457 A1 Jun. 23, 2005

(30) Foreign Application Priority Data

Dec. 22, 2003 (JP) ................................ 2003-425105
Nov. 5, 2004 (JP) ................................ 2004-322796

(51) Int. Cl.
*A61B 1/04* (2006.01)
*A61B 1/00* (2006.01)
*A61M 29/00* (2006.01)

(52) U.S. Cl. .................. 600/116; 600/115; 604/101.03; 604/102.01

(58) Field of Classification Search .................. 600/101, 600/113–116, 120, 155; 604/27, 43, 45, 604/57, 101.02–101.04, 103.05, 164.11, 604/500, 102.01–102.03, 101.01, 101.05; 606/108

See application file for complete search history.

(56) References Cited

U.S. PATENT DOCUMENTS

| 3,057,345 | A | * | 10/1962 | Ferris et al. .................. 600/116 |
| 4,040,413 | A | * | 8/1977 | Ohshiro ........................ 600/116 |
| 4,327,720 | A | * | 5/1982 | Bronson et al. .......... 128/207.15 |
| 4,445,892 | A | * | 5/1984 | Hussein et al. .......... 604/101.05 |
| 4,584,998 | A | * | 4/1986 | McGrail .................. 128/207.15 |
| 5,088,492 | A | * | 2/1992 | Takayama et al. ............ 600/431 |
| 5,143,062 | A | * | 9/1992 | Peckham ................. 128/207.14 |
| 5,460,610 | A | * | 10/1995 | Don Michael ........... 604/101.03 |
| 5,613,947 | A | * | 3/1997 | Chin ......................... 604/103.13 |
| 5,728,134 | A | * | 3/1998 | Barak .......................... 606/214 |
| 6,248,086 | B1 | * | 6/2001 | Sweezer et al. .............. 604/4.01 |
| 6,461,327 | B1 | * | 10/2002 | Addis et al. ............... 604/101.04 |
| 6,569,148 | B2 | * | 5/2003 | Bagaoisan et al. ............ 604/509 |
| 2002/0014238 | A1 | * | 2/2002 | Kotmel ..................... 128/204.18 |
| 2005/0124856 | A1 | * | 6/2005 | Fujikura et al. ............... 600/115 |
| 2005/0222496 | A1 | * | 10/2005 | Sekiguchi ...................... 600/115 |

FOREIGN PATENT DOCUMENTS

| JP | 10-155733 A | 6/1998 |
| JP | 10-248794 | 9/1998 |
| JP | 10-248794 A | 9/1998 |
| JP | 2001-340462 | 12/2001 |
| JP | 2002-301019 | 10/2002 |
| JP | 2002-301019 A | 10/2002 |
| JP | 2003-144378 | 5/2003 |

OTHER PUBLICATIONS

Japanese Office Action (and English translation thereof) issued on Jan. 20, 2006.
European Search Report dated Apr. 4, 2005.

* cited by examiner

*Primary Examiner* — Anhtuan Nguyen
*Assistant Examiner* — Alireza Nia
(74) *Attorney, Agent, or Firm* — Harness, Dickey & Pierce, P.L.C.

(57) ABSTRACT

An insertion assisting tool for an endoscope which is a tubular insertion assisting tool which is provided with an inflatable and deflatable balloon attached to a tip end outer peripheral part, and through which an insertion section for an endoscope is capable of being inserted, comprising:
an air hole formed at an outer periphery and/or a tip end part of the insertion assisting tool.

13 Claims, 5 Drawing Sheets

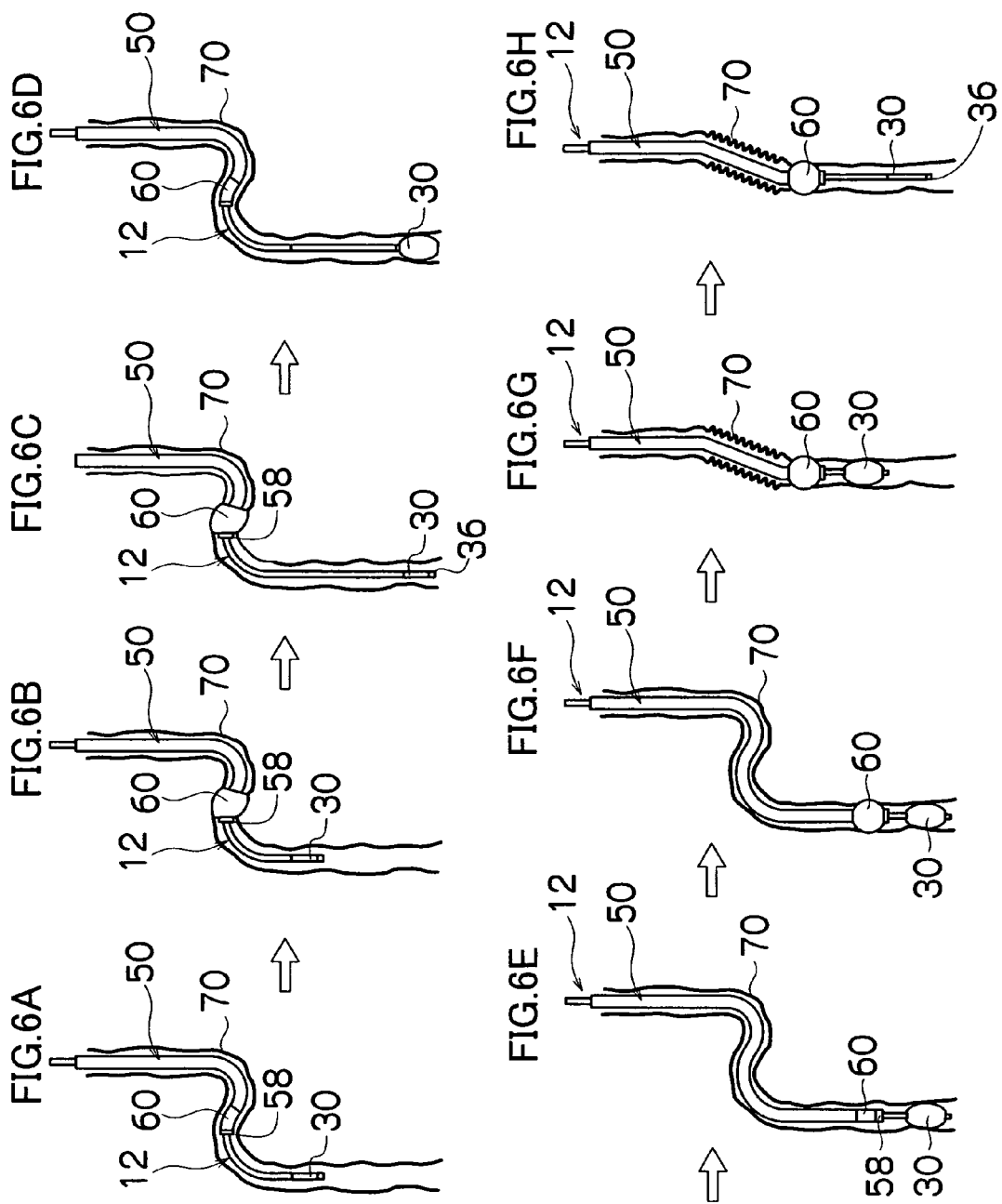

INSERTION ASSISTING TOOL FOR ENDOSCOPE AND ENDOSCOPE OPERATING METHOD

BACKGROUND OF THE INVENTION

1. Field of the Invention

The present invention relates to an insertion assisting tool including a balloon at a tip end outer peripheral portion, and a double balloon type insertion assisting tool for an endoscope, which is fitted onto an endoscope insertion section also including a balloon at a tip end outer peripheral portion and guides the endoscope insertion section into a body cavity, and an endoscope operation method.

2. Description of the Related Art

When the insertion section of an endoscope is inserted into a deep alimentary canal such as a small intestine, by only pushing the insertion section into the deep alimentary canal, the force is difficult to transmit to a tip end of the insertion section due to complicated bending of an intestinal canal, and insertion into a deep part is difficult. Namely, if excessive bending and deflection occur to the insertion section, it is difficult to insert the insertion section further into a deeper part. Thus, there is proposed an endoscope apparatus which prevents excessive bending and deflection of the insertion section by inserting the insertion section into a body cavity with an insertion assisting tool called an over tube or a sliding tube attached to the insertion section of the endoscope, and guiding the insertion section with this insertion assisting tool (for example, Japanese Patent Application Publication No. 10-248794).

Meanwhile, a double balloon type endoscope apparatus disclosed in Japanese Patent Application Publication No. 2002-301019 includes an endoscope with a first inflatable and deflatable balloon attached to a tip end outer peripheral portion of an endoscope insertion section, and an over tube which serves as a guide at the time of insertion of the insertion section, with a second inflatable and deflatable balloon attached to the tip end peripheral portion, and the endoscope insertion section inserted into the over tube. This double balloon type endoscope apparatus is for inserting the endoscope insertion section into a deep part of an alimentary canal by carrying out an inserting operation of the over tube and the endoscope insertion section and the inflation and deflation operations of the first and the second balloons in accordance with a predetermined procedure.

SUMMARY OF THE INVENTION

However, the double balloon type endoscope apparatus in Japanese Patent Application Publication No. 2002-301019 has the problem that when, for example, the second balloon is inflated and closely fitted to the intestinal wall and thereafter, an operation of moving the over tube in the extracting direction is performed, the over tube cannot be smoothly moved. Namely, this is considered to result from addition of compression to the air stored at a base end part side of the over tube with respect to the second balloon (air stored in a gap between the over tube and the intestinal wall) by the operation of the over tube, and the air pressure caused by this gives a difficulty to the extracting operation of the over tube.

The present invention is made in view of the above circumstances, and has its object to provide an insertion assisting tool for an endoscope and an endoscope operation method capable of smoothly performing an extracting operation of the insertion assisting tool in the state in which a balloon of the insertion assisting tool is inflated.

In order to attain the above-described object, a first aspect of the present invention is an insertion assisting tool for an endoscope which is a tubular insertion assisting tool, which is provided with an inflatable and deflatable balloon attached to a tip end outer peripheral portion, and through which an insertion section of an endoscope is capable of being inserted, comprising an air hole formed at an outer periphery and/or a tip end part of the insertion assisting tool.

A second aspect of the present invention is the insertion assisting tool for an endoscope according to the first aspect, wherein the endoscope insertion section includes an inflatable and deflatable balloon at a tip end part of the endoscope insertion section.

In order to attain the above-described object, a third aspect of the present invention is, in an endoscope operating method of combining an endoscope including a first inflatable and deflatable balloon at an insertion section tip end part, and a tubular insertion assisting tool, which is provided with a second inflatable and deflatable balloon attached to a tip end outer peripheral part, and through which the insertion section is capable of being inserted, and inserting the endoscope into a region to be observed under each operation of inflating and deflating operations of the first balloon and the second balloon, an inserting operation of the insertion part by insertion guide by the insertion assisting tool, and an inserting operation of the insertion assisting tool for guiding insertion of the insertion section, including the steps of performing an operation of supplying air via an air hole formed at an outer periphery and/or a tip end part of the insertion assisting tool at a time of the inserting operation, and discharging air via the air hole at a time of extracting operation of the endoscope insertion section and/or the insertion assisting tool.

According to the present invention, when the extracting operation of the insertion assisting tool in the state in which the balloon of the insertion assisting tool is inflated, the air stored in the gap between the insertion assisting tool and the intestinal wall flows from the air hole of the insertion assisting tool, and is discharged to the outside via the insertion assisting tool. Thereby, at the time of extracting operation of the insertion assisting tool, the air pressure is not exerted on the insertion assisting tool, and therefore, the extracting operation of the insertion assisting tool can be performed smoothly.

According to the present invention, the air in the intestinal space sealed between the balloon of the insertion assisting tool and the balloon at the tip end of the endoscope insertion section is discharged to the outside from the air hole via the insertion assisting tool when the air pressure is to rise. Accordingly, air pressure rise in the intestinal space can be prevented, and therefore, influence on the intestinal wall by the air pressure rise can be eliminated.

According to the insertion assisting tool for an endoscope and the endoscope operating method according to the present invention, the air hole is formed at an outer periphery and/or the tip end part of the insertion assisting tool, and therefore, the extracting operation of the insertion assisting tool in the state in which the balloon of the insertion assisting tool is inflated can be performed smoothly.

BRIEF DESCRIPTION OF THE DRAWINGS

FIGS. 6A to 6H are explanatory views showing an operation method of the endoscope apparatus shown in FIG. 1.

DETAILED DESCRIPTION OF THE PREFERRED EMBODIMENTS

A preferred embodiment of an insertion assisting tool for an endoscope and an endoscope operation method according to the present invention will be explained in accordance with the following attached drawings.

Figure 1:
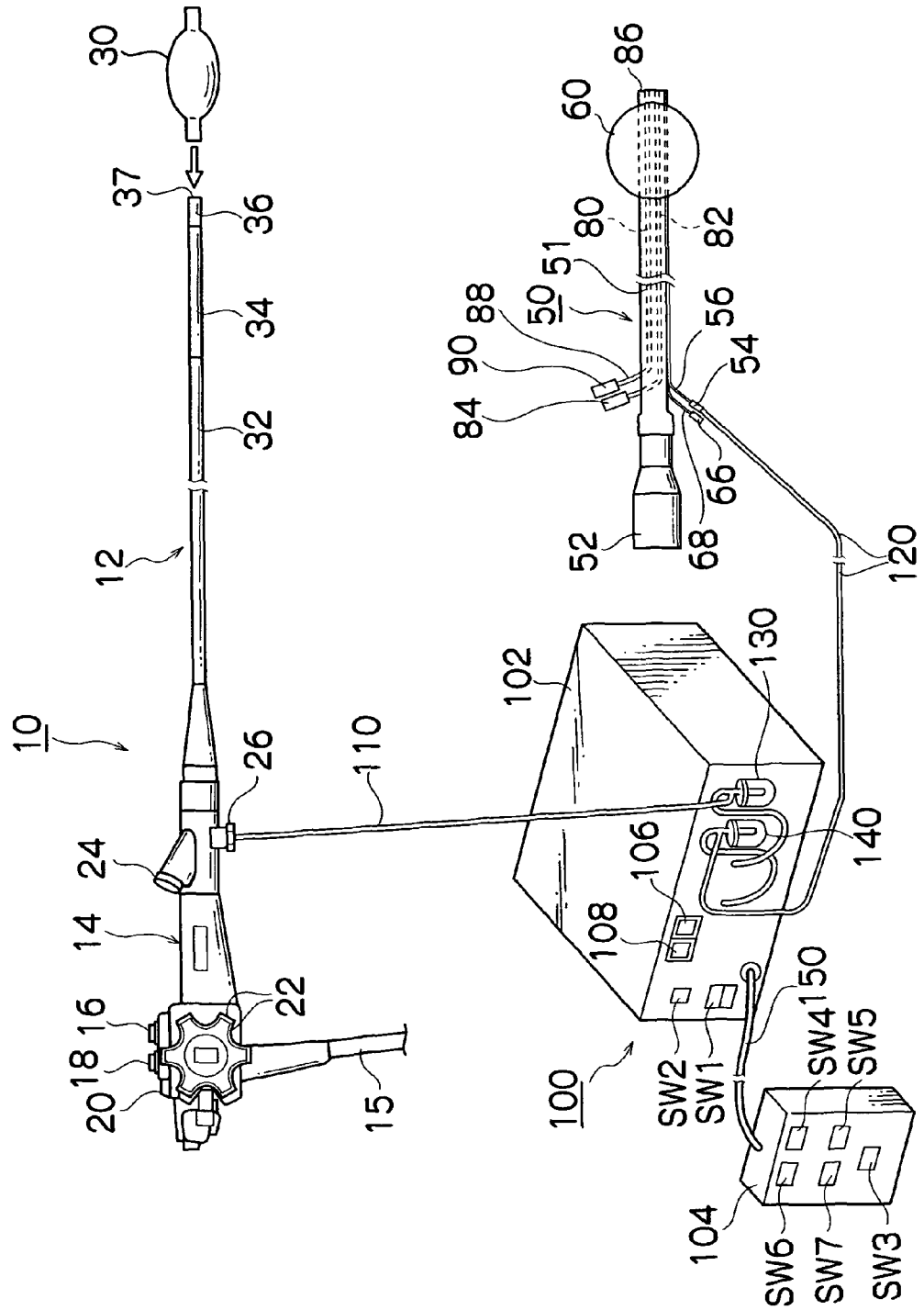
FIG. 1 is a system schematic diagram of an endoscope apparatus to which an over tube according to the present invention is applied.

FIG. 1 shows a system schematic diagram of an endoscope apparatus to which an insertion assisting tool according to the present invention is applied. The endoscope apparatus shown in the drawing is constructed by an endoscope 10, an over tube (corresponding to the insertion assisting tool) 50, and a balloon control device 100.

The endoscope 10 includes a hand operation section 14, and an insertion section 12 connected to the hand operation section 14. A universal cable 15 is connected to the hand operation section 14, and a connector (not shown) connected to a processor and a light source device not shown is provided at a tip end of the universal cable 15.

An air/water passing button 16, a suction button 18, and a shutter button 20 which are operated by an operator are provided in parallel on the hand operation section 14, and a pair of angle knobs 22 and 22, and the forceps insertion part 24 are provided respectively at predetermined positions. Further, the hand operation section 14 is provided with a balloon air port 26 for supplying air to a first balloon 30 and sucking air from the first balloon 30.

The insertion section 12 is constructed by a flexible part 32, a curving part 34 and a tip end rigid part 36. The curving part 34 is constructed by connecting a plurality of node rings to be able to curve, and is remotely operated to curve by the rotational operation of a pair of angle knobs 22 and 22 provided on the hand operation section 14. Thereby, a tip end surface 37 of the tip end rigid part 36 can be faced in a desired direction.

Figure 2:
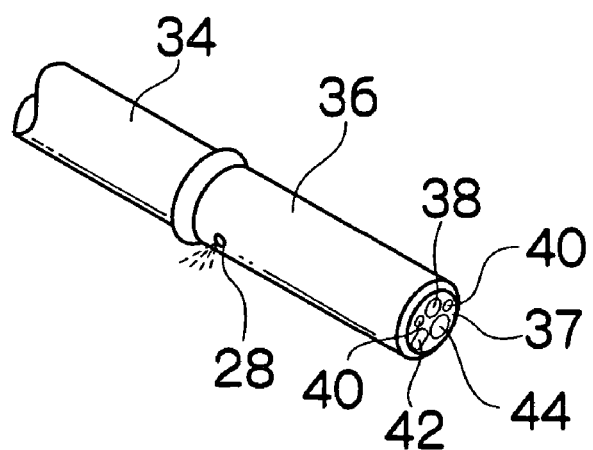
FIG. 2 is a perspective view showing a tip end part of an insertion section of an endoscope.

As shown in FIG. 2, the tip end surface 37 of the tip end rigid part 36 is provided with an object optical system 38, an illumination lens 40, air/water passing nozzle 42, a forceps port 44 and the like in predetermined positions. An air supply/suction port 28 is provided on an outer peripheral surface of the tip end rigid part 36, and this air supply/suction port 28 communicates with the balloon air port 26 in FIG. 1 via an air supply tube (not shown) with an inner diameter of about 0.8 mm which is inserted into the insertion section 12. Accordingly, air is blown out of the air supply/suction port 28 of the tip end rigid part 36 by supplying air to the balloon air port 26, and on the other hand, air is sucked from the air supply/suction port 28 by sucking air from the balloon air port 26.

Figure 3:
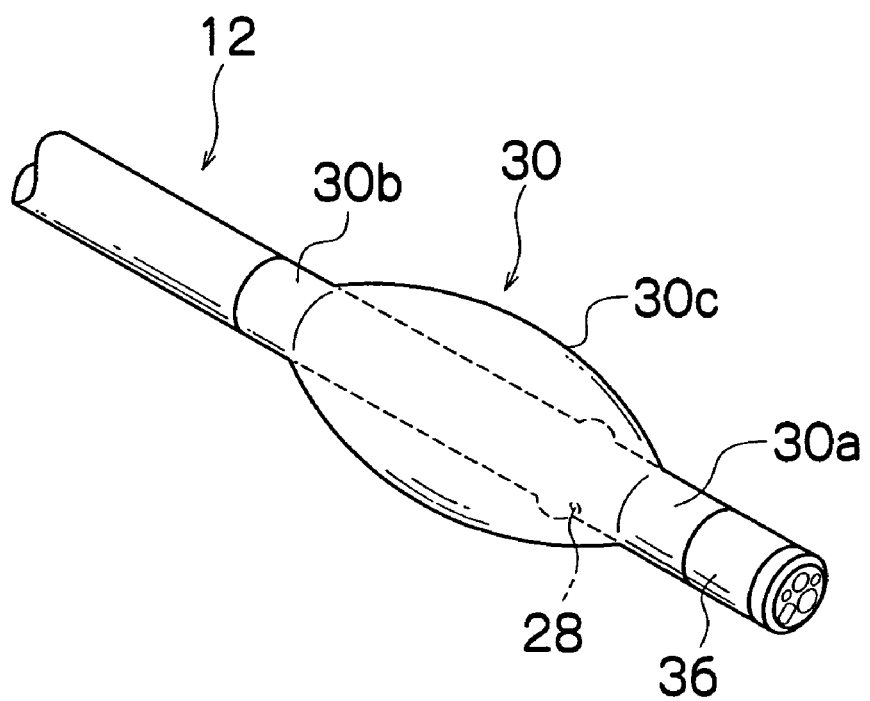
FIG. 3 is a perspective view showing the tip end rigid part of the insertion section onto which a first balloon is fitted.

As shown in FIG. 1, the first balloon 30 constituted of an elastic body such as rubber is detachably attached to the tip end rigid part 36 of the insertion section 12. The fist balloon 30 is formed by a bulging portion 30c in a center and attaching portions 30a and 30b at both ends of the bulging portion 30c, and is attached to the tip end rigid part 36 side so that the air supply/suction port 28 is located inside the bulging portion 30c as shown in FIG. 3. The attaching portions 30a and 30b are formed to have smaller diameters than the diameter of the tip end rigid portion 36, and after being closely fitted onto the tip end part 36 with their elastic forces, the attaching portions 30a and 30b are fixed with threads not shown wound around the attaching portions 30a and 30b. The fixation is not limited to the thread winding fixation, but the attaching portions 30a and 30b may be fixed to the tip end rigid part 36 by fitting fixing rings onto the attaching portions 30a and 30b.

The first balloon 30 fitted onto the tip end rigid part 36 has its bulging portion 30c inflated in a substantially spherical shape by blowing air from the air supply/suction port 28 shown in FIG. 2. On the other hand, by sucking air from the air supply/suction port 28, the bulging portion 30c is deflated and is closely fitted onto the outer peripheral surface of the tip end rigid part 36.

Figure 4:
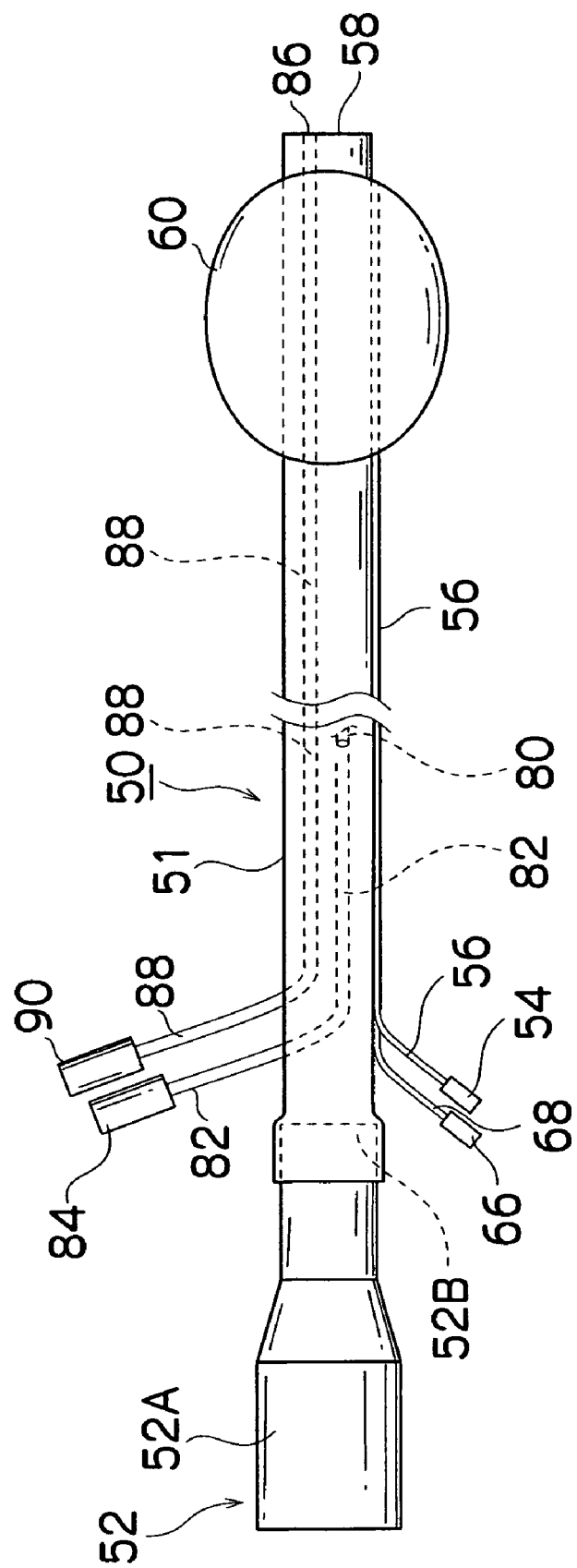
FIG. 4 is a side view of an over tube.
Figure 5:
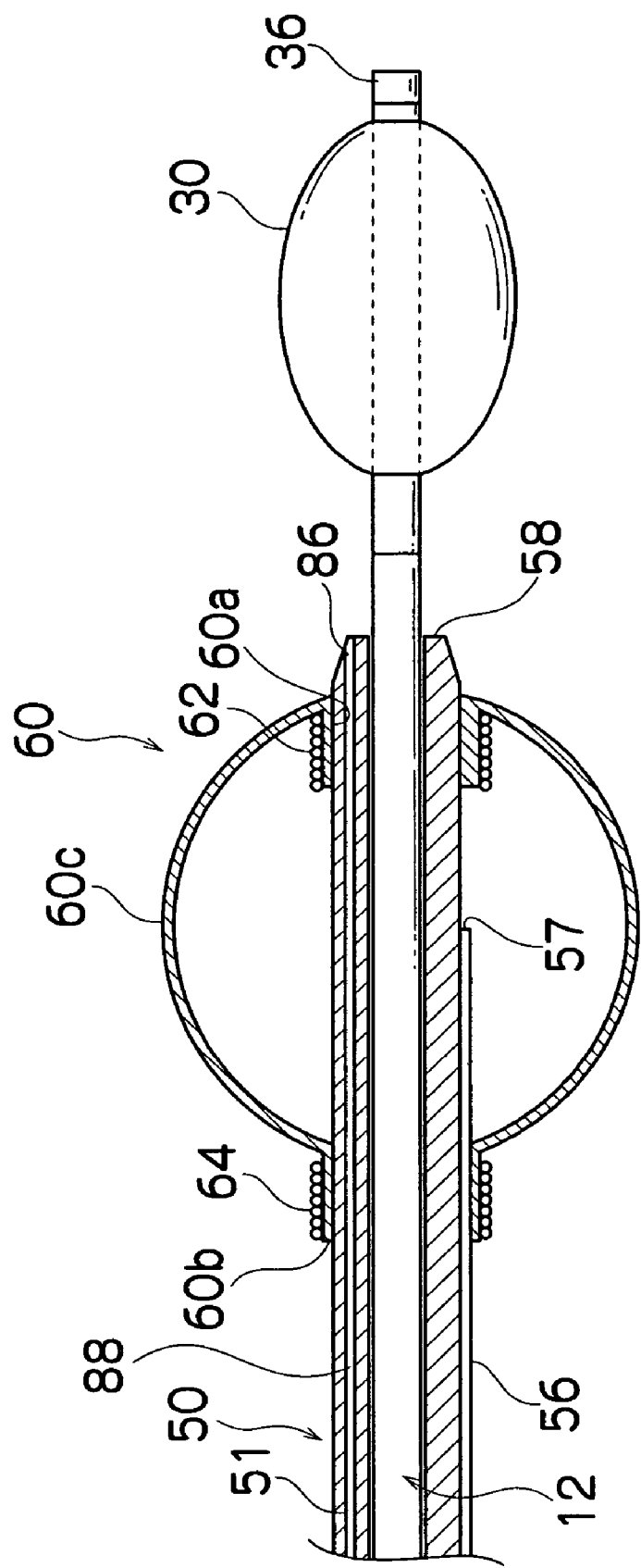
FIG. 5 is a sectional side view showing a tip end part of the over tube through which the insertion section is inserted.

The over tube 50 shown in FIG. 1 is constructed by a tube body 51, and a gripping part 52. The tube body 51 is formed into a cylindrical shape and has a slightly larger inner diameter than an outer diameter of the insertion section 12, as shown in FIGS. 4 and 5. The tube body 51 is constructed by covering an outer side of a flexible resin tube made of urethane or the like with lubricating coat and covering an inner side with the lubricating coat.

The gripping part 52 is formed into a cylindrical shape as shown in FIG. 4, and constructed by a body portion 52A having a large diameter which is gripped by an operator, and a connecting portion 52B fitted onto the base end part of the tube body 51. The insertion section 12 of the endoscope 10 shown in FIG. 1 is inserted toward the tube body 51 from the body portion 52A of the gripping part 52 shown in FIG. 4.

A balloon air port 54 is provided at the base end side of the tube body 51. An air supply tube 56 with an inner diameter of about 1 mm is connected to the balloon air port 54, and this tube 56 is bonded to an outer peripheral surface of the tube body 51 and is provided to extend to a tip end portion of the tube body 51 as shown in FIG. 5.

A tip end 58 of the tube body 51 is formed into a tapered shape. A second balloon 60 constituted of an elastic body such as rubber is fitted onto the base end side of the tip end 58 of the tube body 51. The second balloon 60 is fitted in the state in which the tube body 51 penetrates through the balloon 60 as shown in FIG. 5, and is constructed by a bulging portion 60c in a center, and attaching portions 60a and 60b at both ends of the bulging portion 60c. The attaching portion 60a at the tip end side is folded back to the inside of the bulging portion 60c, and the attaching portion 60a folded back is fixed to the tube body 51 with an X-ray contrast thread 62 wound around the attaching portion 60a which is folded back. The attaching portion 60b at the base end side is disposed outside the second balloon 60, and is fixed to the tube body 51 with a thread 64 wound around the attaching portion 60b.

The bulging portion 60c is formed into a substantially spherical shape in a natural state (the state in which the bulging portion 60c does not inflate or deflate), and as for the size, the bulging portion 60c is formed to be larger than the size of the first balloon 30 in a natural state (the state in which the balloon 30 does not inflate or deflate). Accordingly, when the air is supplied to the first balloon 30 and the second balloon 60 at the same pressure, the outer diameter of the bulging portion 60c of the second balloon 60 becomes larger than the outer diameter of the bulging portion 30c of the first balloon 30. The outer diameter of the second balloon 60 is constructed so as to be φ50 mm when the outer diameter of the first balloon 30 is φ25 mm, for example.

The aforementioned tube 56 is opened in the inside of the bulging portion 60c, and the opening is formed as an air supply/suction port 57. Accordingly, when air is supplied from the balloon air port 54, the air is blown from the air supply/suction port 57 and thereby, the bulging portion 60c is inflated. When air is sucked from the balloon air port 54, the air is sucked from the air supply/suction portion 57, and the second balloon 60 is deflated.

Reference numeral 66 in FIG. 4 designates an inlet port for filling a lubricating liquid such as water into the tube body 51, and the inlet port 66 communicates with the base end part side of the tube body 51 via a tube 68 with a thin diameter.

Incidentally, in the over tube 50 in this embodiment, an air release hole (air hole) 80 is formed at a base end part side from the second balloon attaching position of the tube body 51. This air release hole 80 is opened as a suction hole 84 at the base end part of the tube body 51 via an air tube 82 integrally formed at or bonded to the tube body 51. In the over tube 5 shown in FIG. 4, the example in which the air release hole 80 is formed at only one location, but a plurality of air release holes 80 may be formed, and the forming position may be any position if only it is at the base end part side from the second balloon attaching position. This air release hole 80 has the function of releasing air stored between the tube body 51 and the intestinal canal (not shown), and therefore, it is preferable to form the air release holes 80 equidistantly around the tube body 51 and at equal spaces in the axial direction.

In the over tube 50, an air release hole (air hole) 86 is formed at the tip end part side from the second balloon attaching position of the tube body 51. This air release hole 86 is opened at the base end part of the tube body 51 as a suction port 90 via an air tube 88 integrally formed at or bonded to the tube body 51. As a result, the air in an intestinal space sealed between the second balloon 60 and the first balloon 30 is discharged from the air release hole 86 to outside air from the suction port 90 at the base end part of the tube body 51 via the air tube 88.

Meanwhile, the balloon control device 100 in FIG. 1 is the device which supplies and sucks fluid such as air to and from the first balloon 30, and supplies and sucks fluid such as air to and from the second balloon 60. The balloon control device 100 is constructed by a device body 102 including a pump, sequencer and the like not shown, and a hand switch 104 for remote control.

A front panel of the device body 102 is provided with a power supply switch SW1, a stop switch SW2, a pressure gauge 106 for the first balloon 30 and a pressure gauge 108 for the second balloon 60. A tube 110 for supplying/sucking air to and from the first balloon 30, and a tube 120 for supplying/sucking air to and from the second balloon 60 are attached to the front panel of the device body 102. Liquid storing tanks 130 and 140 for storing body fluid, which flows backward from the first balloon 30 and the second balloon 60 when the first balloon 30 and the second balloon 60 are broken, are respectively provided at midpoints of the respective tubes 110 and 120.

Meanwhile, the hand switch 104 is provided with a similar stop switch SW3 to the stop switch SW2 at the side of the device body 102, an ON/OFF switch SW4 for supporting pressurization/decompression of the first balloon 30, a pose switch SW5 for keeping the pressure of the first balloon 30, an ON/OFF switch SW6 for supporting pressurization/decompression of the second balloon 60, and a pose switch SW7 for keeping the pressure of the second balloon 60. This hand switch 104 is electrically connected to the device body 102 via a cable 150.

The balloon control device 100 which is constructed as above supplies air to the first balloon 30 and the second balloon 60 and inflates the first balloon 30 and the second balloon 60, and controls the air pressure at a fixed value to keep the first balloon 30 and the second balloon 60 in the inflated state. The balloon control device 100 sucks air from the first balloon 30 and the second balloon 60 and deflates the first balloon 30 and the second balloon 60, and controls the air pressure at a fixed value to keep the first balloon 30 and the second balloon 60 in the deflated state.

Next, an operation method of the endoscope apparatus will be explained in accordance with FIGS. 6A to 6H.

First, as shown in FIG. 6A, the insertion section 12 is inserted into an intestinal canal (for example, descending limb of duodenum) 70 in the state in which the over tube 50 covers the insertion section 12. At this time, the first balloon 30 and the second balloon 60 are deflated.

Next, as shown in FIG. 6B, in the state in which the tip end 58 of the over tube 50 is inserted into a bent portion of the intestinal canal 70, air is supplied to the second balloon 60 to inflate the second balloon 60. As a result, the second balloon 60 is closely fitted to and caught by the intestinal canal 70, and the tip end 58 of the over tube 50 is fixed to the intestinal canal 70.

Next, as shown in FIG. 6C, only the insertion section 12 of the endoscope 10 is inserted to a deep part of the intestinal canal 70 with the over tube 50 as a guide. Then, as shown in FIG. 6D, air is supplied to the first balloon 30 to inflate the first balloon 30. As a result, the first balloon 30 is closely fitted and fixed to the intestinal canal 70. In this case, the first balloon 30 is smaller in the size at the time of inflation than the second balloon 60, and therefore the burden exerted on the intestinal canal 70 is small, thus making it possible to prevent damage to the intestinal canal 70.

Next, after air is sucked from the second balloon 60 to deflate the second balloon 60, the over tube 50 is pushed in, and inserted along the insertion section 12, as shown in FIG. 6E. Then, after the tip end 58 of the over tube 50 is pushed into the vicinity of the first balloon 30, air is supplied to the second balloon 60 to inflate the second balloon 60 as shown in FIG. 6F. As a result, the second balloon 60 is closely fitted and fixed to the intestinal canal 70. Namely, the intestinal canal 70 is gripped by the second balloon 60.

Next, as shown in FIG. 6G, the operation of drawing in the intestinal canal 70 by operating the over tube 50 in the drawing direction is performed. Thereby, the intestinal canal 70 contracts substantially straight, and excessive deflection and bending of the over tube 50 are eliminated. When the over tube 50 is drawn in at this time, both the first balloon 30 and the second balloon 60 are caught in the intestinal canal 70, but the friction resistance of the first balloon 30 is smaller than the friction resistance of the second balloon 60. Therefore, even if the first balloon 30 and the second balloon 60 move to separate from each other, the first balloon 30 with small friction resistance slides with respect to the intestinal canal 70, and therefore, it does not happen that the intestinal canal 70 is damaged by being pulled by both the balloons 30 and 60.

At this time, the air stored in the gap between the tube body 51 and the intestinal wall flows in from the air release hole 80 (see FIG. 4) of the tube body 51, and is discharged to the outside air from the suction port 84 formed at the base end part of the tube body 51 via the air tube 82. As a result, at the time of the operation of the over tube 50 in the drawing direction, the air pressure occurring as a result that the air stored in the gap between the over tube 50 and the intestinal wall is compressed is not exerted on the over tube 50, and therefore, the operation of the over tube 50 in the drawing direction can be performed smoothly. The stored air can be discharged by opening the suction port 84 to atmosphere, but a manual suction tool such as an injector is connected to the suction port 84, and the air may be forcefully discharged by the manual suction tool.

Next, as shown in FIG. 6H, air is sucked from the first balloon 30 to deflate the first balloon 30. Then, the tip end rigid part 36 of the insertion section 12 is inserted into as deep a part of the intestinal canal 70 as possible. Namely, the inserting operation as shown in FIG. 6C is performed again. Thereby, the tip end rigid part 36 of the insertion section 12 can be inserted into a deep part of the intestinal canal 70. When the insertion section 12 is further inserted into a deep part, the pushing operation as shown in FIG. 6E is performed after the fixing operation as shown in FIG. 6D is performed, the gripping operation as shown in FIG. 6F and the drawing operation as shown in FIG. 6G, and the inserting operation as shown in FIG. 6H are repeatedly performed in sequence. Thus, the insertion section 12 can be further inserted into a deep part of the intestinal canal 70.

In the over tube 50 of the embodiment, the air release hole 86 is formed at the tip end part side from the second balloon attaching position of the tube body 51, and therefore, when the air pressure in the sealed intestinal space between the second balloon 60 and the first balloon 30 is to rise during the above operation, the air in the intestinal space is discharged from the air release hole 86 to the outside air from the suction port 90 formed at the base end part of the tube body 51. Accordingly, rise in the air pressure in the intestinal space can be prevented, and therefore, influence on the intestinal wall by the rise in the air pressure can be eliminated.

As an example of the operation method of the endoscope apparatus, there is the operation method of inserting the insertion section 12 and the over tube 50 into the intestinal canal 70 while inflating the intestinal canal 70 by injecting air from the air/water passing nozzle 42 after inserting the endoscope insertion section 12 into the intestine canal 70.

When the drawing operation of the intestinal canal 70 by the over tube 50 shown in FIG. 6G is carried out after the above operation, the air does not sufficiently released when the intestinal canal 70 is to be drawn in since the air is inside the intestinal canal 70, thus causing the phenomena in which the air is stored in some mid point in some cases. In such a case, the air stored in the intestinal canal 70 can be discharged from the air release hole 86 according to the over tube 50 in which the air release hole 86 is formed at the tip end part side of the tube body 51 of the over tube 50, and therefore, storing of air at the time of drawing in the intestinal canal 70 can be prevented.

In this embodiment, the over tube 50 is shown as an example as the insertion assisting tool, but the present invention is not limited to this, and a sliding tube which is inserted per anus can be used.

What is claimed is:

1. An endoscope apparatus having an insertion assisting tool to be inserted into alimentary canal, comprising:
    an endoscope having an air/water passing button, a suction button and a shutter button operated by an operator provided in a hand operation section, the hand operation section being provided with an air port for supplying/sucking air to a first balloon;
    an insertion tube in which an insertion section of the endoscope is inserted therethrough, the insertion section includes a flexible part, a curving part, and a tip end rigid part, wherein an end surface of the tip end rigid part includes an object optical system, an illumination lens, air/water passing nozzle, and a forceps port, and an air supply/suction port is provided on an outer peripheral surface of the insertion section to communicate with the air port of the endoscope;
    a second balloon of the insertion assisting tool which is attached to the insertion tube at a balloon attaching portion, to inflate/deflate by supplying/sucking air, and capable of being closely fitted onto an alimentary canal wall when inflated; and
    an air hole formed at a proximal end of the balloon attaching portion of the balloon on an external surface of the insertion tube, wherein
    the air hole communicates with an opening formed at a proximal end of the insertion tube through an air discharge channel formed individually to the insertion tube, and
    the air hole is a hole for discharging air stored in a gap formed by the second balloon of the insertion assisting tool, the insertion tube, and the alimentary canal wall during operation in a drawing direction when the alimentary canal is drawn towards the proximal end side by drawing the insertion assisting tool towards the proximal end side in a state in which the second balloon of the insertion assisting tool is inflated.

2. The insertion assisting tool for an endoscope according to claim 1, wherein the endoscope insertion section comprises an inflatable and deflatable balloon at a tip end part of the endoscope insertion section.

3. The insertion assisting tool for an endoscope according to claim 1, wherein the insertion tube has an insertion portion of the endoscope inserted in a state where the insertion portion can be inserted and/or withdrawn.

4. The insertion assisting tool for an endoscope according to claim 1, wherein a plurality of air holes are formed at the balloon attaching portion of the balloon on an external surface of the insertion tube.

5. The insertion assisting tool for an endoscope according to claim 1, wherein a plurality of air holes are formed equidistantly around the insertion tube.

6. The insertion assisting tool for an endoscope according to claim 1, wherein the air hole is connected to a suction source.

7. The insertion assisting tool for an endoscope according to claim 1, wherein the air hole is open to atmosphere.

8. An endoscope apparatus having an insertion assisting tool to be inserted into an alimentary canal, comprising:
    an endoscope having an air/water passing button, a suction button and a shutter button operated by an operator provided in a hand operation section, the hand operation section being provided with an air port for supplying/sucking air to a first balloon;
    an insertion tube in which an insertion portion of the endoscope having the first balloon at a tip end of the insertion portion thereof, which inflates/deflates by supplying/sucking air and capable of being closely fitted onto a wall of the alimentary canal when inflated, is inserted, the insertion section includes a flexible part, a curving part, and a tip end rigid part, wherein an end surface of the tip end rigid part includes an object optical system, an illumination lens, air/water passing nozzle, and a forceps port;
    a second balloon of the insertion assisting tool which is attached to the insertion tube at a balloon attaching portion, to inflate/deflate by supplying/sucking air, and capable of being closely fitted onto the wall of the alimentary canal when inflated, the second balloon draws the alimentary canal during operation of the insertion tube in a drawing direction when inflated; and
    an air hole formed at a position of a distal end of the balloon attaching portion of the insertion tube, wherein
    the air hole communicates through an air discharge channel formed separately from the insertion tube, and
    the air hole is a hole for discharging air stored in a gap formed between the first and the second balloons by the insertion tube and the alimentary canal wall during operation of the insertion tube in a drawing direction when the alimentary canal is drawn towards the proximal end side by drawing the insertion assisting tool towards the proximal end side in a state in which the first and the second balloon are inflated.

9. The insertion assisting tool for an endoscope according to claim 8, wherein the insertion tube has an insertion portion of the endoscope inserted in a state where the insertion portion can be inserted and/or withdrawn.

10. The insertion assisting tool for an endoscope according to claim 8, wherein a plurality of air holes are formed at the balloon attaching portion of the balloon on an external surface of the insertion tube.

11. The insertion assisting tool for an endoscope according to claim 8, wherein a plurality of air holes are formed equidistantly around the insertion tube.

12. The insertion assisting tool for an endoscope according to claim 8, wherein the air hole is connected to a suction source.

13. The insertion assisting tool for an endoscope according to claim 8, wherein the air hole is open to atmosphere.

* * * * *